(12) United States Patent
Withrow, III et al.

(10) Patent No.: US 8,920,725 B2
(45) Date of Patent: Dec. 30, 2014

(54) PORTABLE APPARATUS FOR IMPROVED SAMPLE ANALYSIS

(75) Inventors: Edward W. Withrow, III, Santa Barbara, CA (US); Jorn Gorlach, Manchester, NJ (US)

(73) Assignee: Montecito Bio-Sciences, Ltd., Montecito, CA (US)

( * ) Notice: Subject to any disclaimer, the term of this patent is extended or adjusted under 35 U.S.C. 154(b) by 300 days.

(21) Appl. No.: 13/248,307

(22) Filed: Sep. 29, 2011

(65) Prior Publication Data

US 2012/0020837 A1 Jan. 26, 2012

Related U.S. Application Data

(63) Continuation of application No. 11/924,033, filed on Oct. 25, 2007, now abandoned.

(60) Provisional application No. 60/863,241, filed on Oct. 27, 2006.

(51) Int. Cl.

| G01N 33/53 | (2006.01) |
|---|---|
| A61B 5/00 | (2006.01) |
| A61B 5/145 | (2006.01) |
| G06F 19/00 | (2011.01) |
| A61B 5/1455 | (2006.01) |
| B01L 3/00 | (2006.01) |

(52) U.S. Cl.
CPC ............ *A61B 5/1455* (2013.01); *B01L 3/5023* (2013.01); *A61B 5/411* (2013.01); *A61B 5/416* (2013.01); *A61B 5/14546* (2013.01); *A61B 5/418* (2013.01); *A61B 5/0002* (2013.01); *G06F 19/3406* (2013.01); *A61B 5/415* (2013.01); *A61B 5/14532* (2013.01); *Y10S 435/809* (2013.01)

USPC .......... 422/68.1; 422/401; 422/420; 422/565; 422/566; 435/809; 435/287.2; 435/287.7; 436/169

(58) Field of Classification Search
USPC ......................................................... 422/425
See application file for complete search history.

(56) References Cited

U.S. PATENT DOCUMENTS

| 4,797,260 | A | 1/1989 | Parker | |
|---|---|---|---|---|
| 5,137,691 | A | 8/1992 | Parker | |
| 6,274,384 | B1 | 8/2001 | Starzl et al. | |
| 6,495,373 | B1 * | 12/2002 | Mauchan | 436/165 |
| 6,964,862 | B2 | 11/2005 | Chen | |
| 7,041,206 | B2 | 5/2006 | Gephart et al. | |
| 2001/0051377 | A1 | 12/2001 | Hammer et al. | |
| 2004/0126899 | A1 | 7/2004 | Lee et al. | 436/518 |
| 2004/0166590 | A1 * | 8/2004 | Green et al. | 436/180 |

(Continued)

OTHER PUBLICATIONS

Supplemental EPO Search Report, Oct. 26, 2011, EPO.

*Primary Examiner* — Jill Warden
*Assistant Examiner* — Benjamin Whatley
(74) *Attorney, Agent, or Firm* — Licata & Tyrrell P.C.

(57) ABSTRACT

The present invention is an improved apparatus for sample analysis. The apparatus employs an assay component containing a membrane having one or a plurality of analyte-specific binding agents attached thereto, a means for absorbing liquid, and a piston means for drawing analytes through said membrane into said means for absorbing liquid. The apparatus is configured to be portable and provide a detector for detecting binding of an analyte to an analyte-specific binding agent, a plurality of data acquisition components, and a computer for integrating, analyzing and storing the detected analyte specific binding and acquired data.

2 Claims, 2 Drawing Sheets

(56) References Cited

U.S. PATENT DOCUMENTS

2006/0222567 A1 10/2006 Kloepfer et al.
2006/0228256 A1 10/2006 McDevitt et al.
2006/0234315 A1 10/2006 MacFadyen et al.
2007/0009381 A1 1/2007 Schulat et al.
2007/0231209 A1 10/2007 Cosentino et al.

* cited by examiner

PORTABLE APPARATUS FOR IMPROVED SAMPLE ANALYSIS

INTRODUCTION

This application is a continuation of U.S. patent application Ser. No. 11/924,033 filed Oct. 25, 2007, now abandoned which claims benefit of priority to U.S. Provisional Patent Application Ser. No. 60/863,241, filed Oct. 27, 2006, the contents of which are incorporated herein by reference in their entireties.

BACKGROUND OF THE INVENTION

Diagnostic testing throughout the world is currently carried out using a variety of different specimen types including whole blood, serum, oral fluid, plasma, cerebrospinal fluid and others. Testing for diseases under laboratory conditions typically involves use of a blood serum specimen obtained by removing the blood cells from an intravenous blood sample by centrifugation. The serum sample so obtained is then tested under laboratory conditions using one of a number of methodologies, such as Enzyme Linked Immuno Sorbent Assay (ELISA), Immunofluorescence (IFA), Latex Agglutination (LA), or any of a number of automated instrument platforms employing chemiluminescence, fluorescence or other sensitive technologies.

One such device for diagnostic testing employs a membrane having a receptor (e.g., an antibody) physically attached to its surface, wherein upon application of a sample, a piston means creates a region of reduced pressure thereby drawing analytes present in the sample through the membrane into a means for absorbing liquid. In this regard, an analyte which specifically binds to the receptor is readily detected. See, e.g., U.S. Pat. No. 4,797,260 and U.S. Pat. No. 5,137,691, incorporated herein by reference in their entireties.

Although serum testing under laboratory conditions has traditionally constituted the technique of choice, there is now a growing trend to move testing closer to the patient so that a patient sample is processed and analyzed more rapidly, often while the patient is still in attendance. The recent advance known as "near-patient" or "point-of-care" testing has caused a shift in the way testing is done.

In contrast to conventional testing, which requires a waiting period of anywhere from several hours to weeks, during which the specimens are transported to a centralized laboratory, processed, and results sent to the physician, point-of-care (POC) testing offers the advantage of giving the physician and/or the patient immediate results. POC testing is particularly advantageous in rural locals which may only have one centralized laboratory or countries with limited resources, wherein centralized laboratories do not exist.

In addition to human patient care, there are a variety of other applications for immediate testing capabilities, including veterinary applications, detection of bioterrorism agents, contaminant detection in quality control and environmental sources, and food safety.

While conventional benchtop testing devices such as TARGET ANALYZER (Target System Diagnostics) are known in the art, such devices are not adaptable to a point-of-care setting and require advanced training to read and interpret results. Needed is a portable handheld apparatus for providing a plurality of measurements and data analysis tools for diagnostic, environmental and quality control applications. Moreover, such a device preferably also contains easy turnkey test calibration. The present invention meets this need in the art.

SUMMARY OF THE INVENTION

The present invention is an improved apparatus for sample analysis. The apparatus is of the type having a membrane with an analyte-specific binding agent attached thereto, a means for absorbing liquid, and a piston means for drawing analytes in a sample through the membrane into the means for absorbing liquid. The apparatus further contains a detector for detecting analyte-specific binding to the analyte-specific binding agent, a plurality of data acquisition components for acquiring data, and a computer, wherein the computer integrates, analyzes and stores the detected analyte-specific binding and acquired data thereby facilitating sample analysis. In some embodiments the apparatus contains one or a plurality of analyte-specific binding agents.

DETAILED DESCRIPTION OF THE INVENTION

The present invention is an apparatus composed of a portable hand-held detector/analyzer used in conjunction with an assay component composed of a membrane having an analyte-specific binding agent bound thereto, a means for absorbing liquid, and a piston means for drawing sample analytes through said membrane into said means for absorbing liquid. See, e.g., U.S. Pat. No. 4,797,250. The apparatus provides a detection component, a plurality of data acquisition components, a computer for integrating, analyzing and storing data, and a display screen, which allows for data visualization. In this regard, the instant apparatus can compile, integrate and analyze data from the assay as well as multiple other sources, thereby providing more relevant information to the user.

Figure 1:
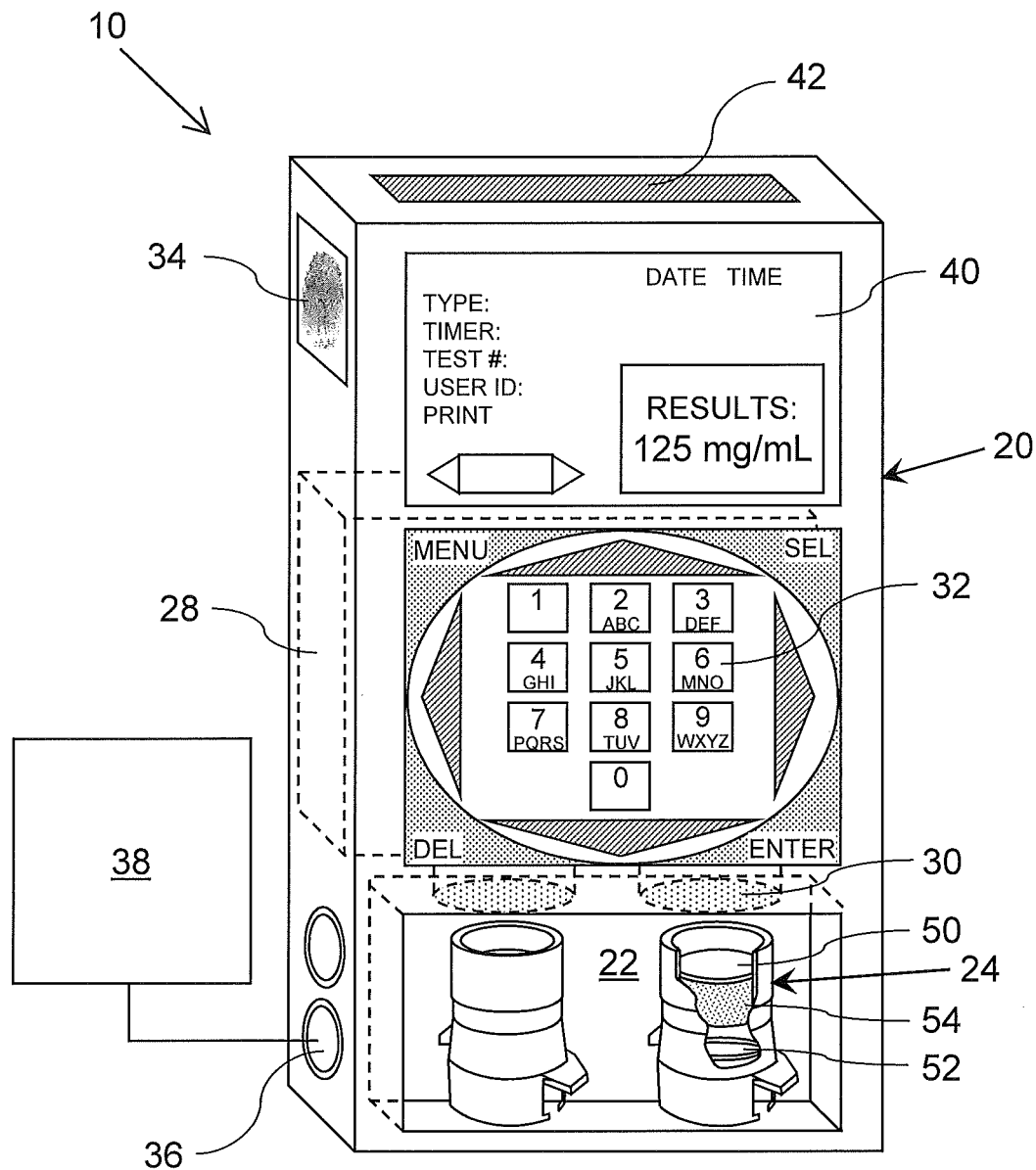
FIG. 1 is an illustration of the portable, hand-held apparatus of the invention.

As illustrated in FIG. 1, apparatus 10 includes housing 20 with chamber 22 for holding removable assay component 24. Housing 20 has disposed therein computer 28 for integrating, analyzing and storing data and detector 30 for detecting binding of the analyte to the analyte-specific binding agent in assay component 24. Manual data acquisition components 32,34 for manually entering data are mounted on housing 20, as is port 36 which provides connectivity with peripheral data acquisition component 38 for acquisition of external data. Visualization of data and other relevant information (e.g., date and/time) is via display screen 40 mounted on housing 20. In some embodiments, apparatus 10 includes output interface 42 (e.g., a SIM card) for data output, such as wired or wireless data transfer interface or printer interface. Desirably, housing 20 has a narrow width such that, apparatus 10 can be held in one hand and operated by the thumb of that same hand or using the free hand. Moreover, given the portability of the instant apparatus, housing 20 is made of a material which is durable and water-resistant or water-proof for use in the field. Apparatus 10 is an improvement over existing analyzers as it provides the user not only with the capability to detect binding between the analyte and the analyte-specific binding agent, but it also provides a plurality of data acquisition components 32,34,38, as well as computer 28 for integrating, analyzing and storing data. These and other elements of the instant apparatus are provided in more detail below.

Figure 2:
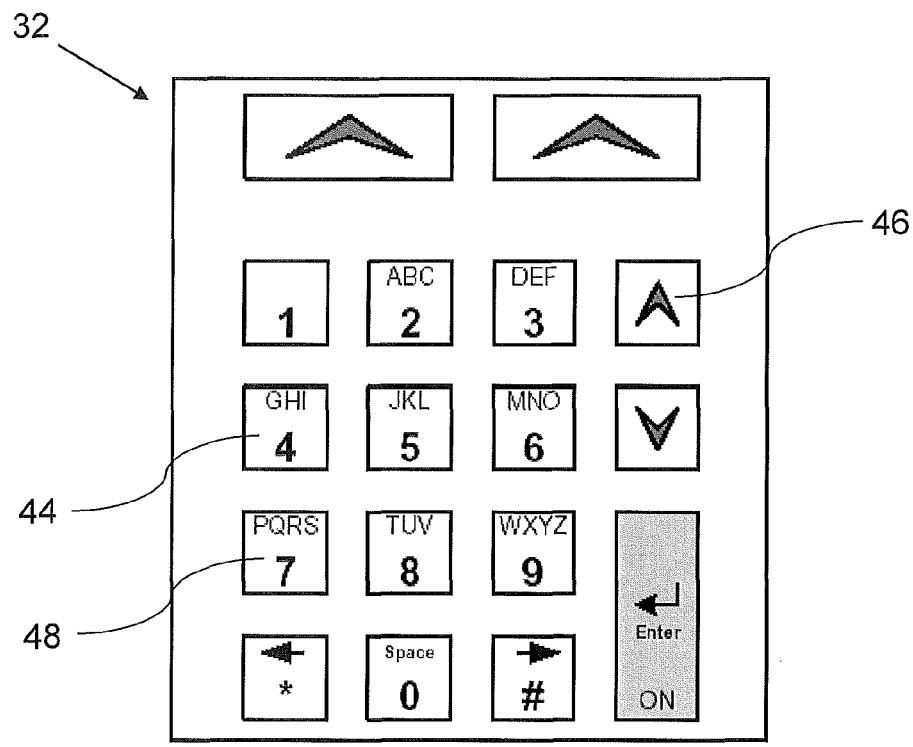
FIG. 2 is an illustration of a keypad for manual data acquisition.

Data Acquisition. Manual input of data such as date, time, user identification (e.g., entry of username or a password), test number, patient information (e.g., name, age, weight, and medical history) can be carried out using one or more manual data acquisition components such as a keypad, touch-pad or microphone/speaker as might be provided with a communicator. A keypad can take any configuration suitable for manually entering data. In general, the keypad can have 10-30 keys with number, letters, or commands associated therewith. As illustrated in FIG. 2, manual data acquisition component 32 is illustrated as a keypad containing seventeen keys 44, including one or more of which are dedicated for a particular purpose 46 or have multiple uses 48, e.g., number and letter entry. As an alternative, the instant analyzer can contain touch-pads (or touch-sensitive areas) or icons on a display screen, which can be touched by the user to enter data. Those touch-pad areas can be dedicated to a particular purpose (e.g., letters or numbers) or can be changeable based on what is displayed in the area when touched (i.e., the indication on the tab can be changed by the user in a suitable manner to display something other than a keypad). In reference to FIG. 1, the touch-pad areas can be part of display screen 40. As such, display screen 40 includes not only a display structure but also suitable sensors associated therewith which are responsive to touching selected areas of the screen. In some embodiments, the instant analyzer contains one manual data acquisition component. In other embodiments, the instant analyzer contains at least two manual data acquisition components. By way of illustration of this embodiment, FIG. 1 shows manual data acquisition component 32, which is a keypad, and also shows manual data acquisition component 34, which is a biometric fingerprint reader. A biometric fingerprint reader finds application in user verification as well as patient identification. Fingerprint verification and sensors for the same are well-known in the art (see, e.g., U.S. Pat. Nos. 7,116,805 and 7,099,497). Manual data acquisition components can be produced from commercially available components well-known to those skilled in the art. Manually entered data can be stored internally or transferred to a printer interface if required for test documentation.

Wired or wireless data transfer from peripheral data acquisition components to the instant apparatus also provides additional data which can be integrated, analyzed, stored, displayed and/or printed. As illustrated in FIG. 1, one or more peripheral data acquisition components 38 can be coupled to apparatus 10 via one or more ports 36, which can provide wired (e.g., USB or ethernet) or wireless connectivity with peripheral data acquisition components 38. Peripheral data acquisition components of use in conjunction with the instant apparatus include servers (e.g., remote or local) which house databases containing patient medical histories or environmental data, as well as any monitor which measures physiological, biological, or environmental conditions. For example, the instant apparatus can obtain data from an electrocardiograph, a heart rate monitor, blood pressure monitors, electronic blood glucose meters, a fetal monitor, a balance, a pH meter, a conductometer, an osmometer, a thermometer, a barometer, a photometer, a luminometer, a radioactivity meter, a carbon dioxide or carbon monoxide meter, a voltmeter, or a device for measuring toxic or volatile organic compounds. A barcode wand or fingerprint reader is also contemplated as a peripheral data acquisition component which can provide, e.g., patient-specific data. One embodiment of the present invention embraces an apparatus with at least one manual data acquisition component and at least one peripheral data acquisition component. Another embodiment of the present invention embraces an apparatus with at least two manual data acquisition components and one peripheral data acquisition component. Additional embodiments of the present invention relate to wireless encrypted data transmission.

Data acquired from the assay component of the instant apparatus can be achieved using any detector. Such data can pertain to the presence or absence of a single analyte in a sample or a plurality of analytes in a sample. In this regard, the membrane of the instant assay component can contain one binding agent or a plurality of binding agents, wherein the term analyte-specific binding agent is intended to include an antibody, an antibody fragment, or an antibody derivative (e.g., an aptamer) which specifically binds to a cognate analyte. Specific binding between two entities generally refers to an affinity of at least $10^6$, $10^7$, $10^8$, $10^9$, or $10^{10}$ $M^{-1}$. Affinities greater than $10^8$ $M^{-1}$ are desired to achieve specific binding.

When the binding agent is an antibody, the antibody can be produced by natural (i.e., immunization) or partial or wholly synthetic means. Antibodies can be monoclonal or polyclonal and include commercially available antibodies, against known, well-characterized analytes. An antibody can be a member of any immunoglobulin class, including any of the human classes: IgG, IgM, IgA, IgD, and IgE. Bispecific and chimeric antibodies are also encompassed within the scope of the present invention. Derivatives of the IgG class, however, are desirable. Further, an antibody can be of human, mouse, rat, goat, sheep, rabbit, chicken, camel, or donkey origin or other species which may be used to produce native or human antibodies (i.e., recombinant bacteria, baculovirus or plants).

For example, naturally-produced monoclonal antibodies can be generated using classical cloning and cell fusion techniques or techniques wherein B-cells are captured and nucleic acids encoding a specific antibody are amplified (see, e.g., U.S. Patent Application No. 20060051348). In such methods, a collection of analytes or an individual analyte (e.g., a peptide or polypeptide) can be used for the initial immunization and in the context of antibody production is referred to herein as the antigen. The antigen of interest is typically administered (e.g., intraperitoneal injection) to wild-type or inbred mice (e.g., BALB/c) or rats, rabbits, chickens, sheep, goats, or other animal species which can produce native or human antibodies. The antigen can be administered alone, or mixed with an adjuvant. After the animal is boosted, for example, two or more times, the spleen or large lymph node, such as the popliteal in rat, is removed and splenocytes or lymphocytes are isolated and fused with myeloma cells using well-known processes, for example, see Kohler and Milstein ((1975) *Nature* 256:495-497) or Harlow and Lane (Antibodies: A Laboratory Manual (Cold Spring Harbor Laboratory, New York (1988)). The resulting hybrid cells are then cloned in the conventional manner, e.g., using limiting dilution, and the resulting clones, which produce the desired monoclonal antibodies, are cultured (see Stewart, S. (2001) Monoclonal Antibody Production. In: *Basic Methods in Antibody Production and Characterization*, Howard and Bethell (eds.), CRC Press, Boca Raton, Fla., pp. 51-67).

Alternatively, antibodies can be derived by a phage display method. Methods of producing phage display antibodies are well-known in the art, e.g., see Huse, et al. ((1989) *Science* 246(4935):1275-81). Selection of antibodies is based on binding affinity to an analyte or analytes of interest.

An antibody fragment encompasses at least a significant portion of the full-length antibody's specific binding ability. Examples of antibody fragments include, but are not limited to, Fab, Fab', F(ab')$_2$, scFv, Fv, dsFv, diabody, Fd fragments or microbodies (see, e.g., U.S. Patent Application No. 20020012909). An antibody fragment can contain multiple chains which are linked together, for instance, by disulfide linkages. A fragment can also optionally be a multi-molecular complex. A functional antibody fragment will typically include at least about 50 amino acid residues and more typically will include at least about 200 amino acid residues. The antibody fragment can be produced by any means. For instance, the antibody fragment can be enzymatically or chemically produced by fragmentation of an intact antibody or it can be recombinantly-produced from a gene encoding the partial antibody sequence. Alternatively, the antibody fragment can be wholly or partially synthetically-produced.

Peptide aptamers which specifically bind to an analyte are, in general, rationally designed or screened for in a library of aptamers (e.g., provided by Aptanomics SA, Lyon, France). In general, peptide aptamers are synthetic recognition molecules whose design is based on the structure of antibodies. Peptide aptamers are composed of a variable peptide loop attached at both ends to a protein scaffold. This double structural constraint greatly increases the binding affinity of the peptide aptamer to levels comparable to that of an antibody (nanomolar range).

Recombinant production of binding agents for the assay component can be achieved using conventional molecular biology techniques and commercially available expression systems. Furthermore, binding agents can be produced using solid-phase techniques (see, e.g., Merrifield J. (1963) *J. Am. Chem. Soc.* 85:2149-2154; Seeberger (2003) *Chem. Commun.* (*Camb*) (10):1115-21). Protein synthesis can be performed using manual techniques or by automation. Automated synthesis can be achieved, for example, using Applied Biosystems 431A Peptide Synthesizer (Perkin Elmer, Boston, Mass.). Various fragments of a binding agent can be chemically-synthesized separately and combined using chemical methods to produce a full-length molecule.

Moreover combinatorial chemistry approaches can be used to produce binding agents (see, e.g., Lenssen, et al. (2002) *Chembiochem.* 3(9):852-8; Khersonsky, et al. (2003) *Curr. Top. Med. Chem.* 3(6):617-43; Anthony-Cahill and Magliery (2002) *Curr. Pharm. Biotechnol.* 3(4):299-315).

To detect, quantify and identify distinct analytes in a sample, the assay component can employ a single or plurality of binding agents. In particular embodiments, a plurality of binding agents is attached to or deposited on the membrane of the assay component in a predetermined pattern. Alternatively stated, the binding agents are arranged in a two-dimensional spatially-resolved configuration so that upon binding to one or more analytes, the presence, quantity, or identity of the one or more analytes can be readily detected. The binding agents can be deposited in a predetermined pattern such as an ordered array composed of rows, columns, spirals, etc. In an alternative embodiment, the plurality of binding agents are deposited in a disordered array.

A plurality of binding agents encompasses 2, 3, 4, 5, 6, 7, 8, 9, 10, 15, 20, 25, 30, 35, 40, or 50 binding agents. In particular embodiments, a plurality of binding agents is 5 or more, 10 or more, 15 or more, 20 or more, 25 or more, or 30 or more binding agents.

It is contemplated that the instant apparatus can also be used in conjunction with an assay component which employs molecular imprinting to bind analytes present in a sample (see, e.g., U.S. Pat. No. 5,821,311).

In the context of the present invention, a membrane is a porous material to which a binding agent can be non-diffusively bound or attached. For example, the porous material can be a thin disk of nitrocellulose, PVDF, or the like. The binding agent can be covalently or non-covalently affixed in or on the membrane by direct deposition, including, but not limited to, airbrushing, ink-jet printing, screen printing, stamping, micropipette spotting, or nanoliter dispensing. Alternatively, the membrane is impregnated with binding agents using the apparatus of U.S. Pat. No. 4,748,042.

An analyte which can be bound by a binding agent includes any compound that can be involved in an antibody:antigen interaction. Typically the analyte will be an antigen, e.g., a protein, a carbohydrate, a cell wall component, lipid, a toxin, a chemical, or a small molecule hapten. It is also possible that the analyte is an antibody that reacts with a bound antigen or an antibody to the antibody.

For instance, an analyte can be a growth factor, a hormone (e.g., progesterone, hCG, or LHRH), a neurotransmitter, a catecholamine, an amino acid (e.g., homocyteine), a cytokine, a lectin, a drug (e.g., cocaine or morphine), a serpin, a protease, a kinase, a phosphatase, a hydrolase, a transcription factor, a heat-shock transcription factor, an inflammatory marker (e.g., C-reactive protein), a cancer marker (e.g., PSA), a cardiac marker (e.g., myoglobin or troponin), a DNA-binding protein, a zinc-finger protein, a leucine-zipper protein, a homeodomain protein, an intracellular signal transduction modulator or effector, an apoptosis-related factor, a DNA synthesis factor, a DNA repair factor, a DNA recombination factor, a cell-surface antigen (e.g., a bacterial proteoglycan), a hepatitis C virus (HCV) protease or HIV protease (e.g., HIV-1 or HIV-2), or a polypeptide isolated from a specific cell, organ or tissue type. In embodiments pertaining to the presence of a particular cell type (e.g., T-cell), virus or microorganism in a sample, the analyte can be associated with the cell, virus or microorganism or partially or wholly extracted from the cell, virus or microorganism. In particular embodiments, the presence or level of an analyte is indicative of a specific disease, disease state or condition, infection or contaminant.

As used herein, a disease or disease state or condition refers to any perturbation of the normal state that results in a change in analyte levels. Examples of perturbations include, but are not limited to, exposure to an allergen; immunological disorders; neoplasms; malignancies; metabolic disorders; all organ and tissue disorders, such as cardiac, liver, prostate, lung, pancreas, skin, eye, nervous system, lymphatic system, colon and breast disorders; aging; dementia; mental disorders; therapeutic drug treatment; drug disorders; pathogen attack; or medical interventions such as grafts, transplants, or pharmacological system treatment.

Advantageously, the instant apparatus can be used in a point-of-care of ambulatory setting to rapidly detect and diagnosis disease, thereby facilitating treatment. For example, medications to prevent heart damage are effective only within a limited number of hours. Yet, because of their risk for excessive bleeding, these medications are given only after a diagnosis of heart attack is made. There are several cardiac markers in blood whose levels rise in the hours following a heart attack and are useful in making the diagnosis of a heart attack. Each cardiac marker raises, peaks, and returns to a normal level according to its own timeline, or diagnostic window. For example, creatine kinase (CK or CPK), an enzyme which is not normally found circulating in the blood, is indicative of muscle or brain damage when present at elevated levels in the blood. Thus, this enzyme is useful for detecting a myocardial infarction (heart attack), muscle disease, or stroke. Similarly, cardiac troponin, a protein that controls the interactions of actin and myosin, is present at very low levels in the blood under normal conditions. However, tropinin levels rise sharply and quickly in response to a heart muscle injury. Therefore, this protein is valuable at detecting mild heart attacks and early detection of other heart problems. Troponin I levels have also been used to help predict a patient's heart attack risk because of their sensitivity and the fact that elevated levels are specific to a heart injury. Myoglobin levels in the blood are also indicative of a heart attack (myocardial infarction) or other muscle damage. When muscle is damaged, as in a heart attack, larger amounts of myoglobin are released and blood levels rise rapidly. Myoglobin has the earliest diagnostic window. It is the first marker to rise after chest pain begins. Myoglobin levels rise within two to three hours, and sometimes as early as 30 minutes. They peak after six to nine hours and return to normal levels within 24-36 hours. Myoglobin tests are sometimes repeated every one to two hours to watch for the rise and peak. C-reactive protein (CRP) is another marker protein indicative of inflammation, including inflammation of the blood vessels. Elevated CRP levels can indicate a risk of future heart attack up to 8 years in advance, even if cholesterol levels are low. Accordingly, an assay component of the present apparatus invention can contain a plurality of binding agents which bind cardiac markers, creatine kinase, cardiac tropinin 1, myoglobin, and CRP, can be used to detect and quantify said markers for diagnosing a heart attack. Advantageously, by using the instant apparatus, data can be acquired from a plurality of data acquisition components (e.g., an assay component as disclosed herein, a heart monitor, and blood pressure monitor) so that a differential diagnosis can be readily made.

It is contemplated that the diagnoses of heart disease, cancer, as well as infectious diseases (e.g., SARS, West Nile virus, *Hantavirus*, Hepatitis A, Hepatitis B, Hepatitis C, HPV, measles, mumps, *rotavirus*, CMV, VZV, Arbovirus, Toxoplasmosis, Malaria, *Chlamydia, H. pylori*, Brucellosis, trichomoniasis, gonorrhea, herpes simplex virus, Lime Disease, Rocky Mountain Spotted Fever, Mad cow, and Asian Bird Flu) can be achieved using the present apparatus. Thus, the instant apparatus finds application in zoological, veterinary and human diagnostic. Additional applications include the differential diagnosis of sexually transmitted disease, wherein the assay component could contain binding agents which bind analytes specific for *Chlamydia*, gonorrhea, and herpes simplex virus. Furthermore, an assay component can be used to bind a variety of drugs (e.g., cocaine, heroin, morphine, etc.) for use in drug screening. The concurrent detection of fruit and vegetable contaminants such as fungal toxins, pesticides, fungicides, or bacteria; meat contaminants such as bacteria or BSE; as well as soil and water contaminants such as pesticides, herbicides, fungicides, toxic pollutants, or bacteria or fungi are also contemplated herein as are detection of bioterrorism agents (e.g., anthrax).

In the use of the instant assay component 24 (FIG. 1), a sample is placed in contact with the membrane 50. After an optimum, predetermined incubation period has passed, a piston means 52 is employed to draw analytes of the sample through the membrane into a means for absorbing liquid 54, and the presence and/or quantity of analytes bound to one or more binding agents on the membrane 50 is determined.

Various means for absorbing liquid are known in the art and can be readily employed including a monolithic solid (e.g., cellulose acetate or POREX) or a granular solid desiccant such as DRIERITE (i.e., anhydrous calcium sulfate) or CELITE (i.e., diatomaceous earth).

Likewise, there are a variety of well-known methods for determining the presence and/or quantity of an analyte bound to a binding agent. For example, a second labeled binding agent which recognizes a distinct epitope on the analyte can be employed. Such a sandwich assay is well-known to those of skill in the art (see, e.g., "Methods in Immunodiagnosis", 2nd Edition, Rose and Bigazzi, eds. John Wiley & Sons, 1980; Campbell et al., "Methods and Immunology", W. A. Benjamin, Inc., 1964; and U.S. Pat. No. 4,376,110). In such assays, the label can be radiometric, fluorometric, enzymatic, colorometric, or any of a number of other labels well-known in the art. It will be appreciated that the instant assay component is not limited to sandwich assays, but also embraces other heterogeneous assays known in the art. However, in the embodiments embracing the binding agents deposited on the membrane in a disordered array, the skilled artisan can appreciate that the detection of at least two analytes will require the use of second labeled binding agents which have distinct labels (e.g., a different fluorescent emission wavelength or color for each analyte to be detected).

In addition to the primary binding agents, and secondary labeled binding agents, the assay can employ a variety of reagents for stabilizing the analyte:binding agent interaction, reagents for increasing the specificity of the analyte:binding agent interaction, as well as washing solutions for removing unbound analytes and unbound secondary labeled binding agents. Similarly, a control binding agent (e.g., anti-horseradish peroxidase) can also be present on the membrane to test if the reagents are working properly, that is, it should always be a positive test if the reagents are added in the correct order. For example, when colorometrically labeled analyte-specific antibodies and colorimetrically labeled control antibody are used, the antibodies can be placed on the membrane to form a pattern. For example, a minus if the test for a particular analyte is negative, or a plus if the test is positive.

To facilitate the quantification of distinct analytes in a sample, the instant assay component can further employ at least two standards for each analyte being detected. As used herein, a standard is a predetermined amount of an analyte being detected, which is provided on the membrane to allow for the quantification of the analyte. The standards are analyzed to produce working curves equating analyte signal with the amount of analyte present in the sample. The amount of analyte present in each sample can then be either judged as elevated relative to other samples, or determined absolutely using the working curve. By way of illustration, 0.1 µg and 10 µg spots of a purified analyte are placed on the membrane prior to use. After the sample is applied and analytes drawn through the membrane, a second, labeled binding agent is applied which binds both the analyte:binding agent complex on the membrane as well as the analyte standards. In this manner, the signals generated by the standards are then used by the apparatus to determine the relative or absolute quantity of the analyte in the sample.

As used herein, the term "sample" includes any biological or environmental material suspected of containing one or more analytes of interest. It is realized that a sample can lack the analyte of interest, or, in other words, the test for that analyte is negative. Biological samples are, e.g., bodily fluids and organic food stuffs, wherein an organic food stuff is intended to include any meat or plant material such as grapes, lettuce, wheat, spinach, etc. A bodily fluid includes whole blood, plasma, serum, sputum, cerebrospinal fluid, pleural fluid, urine and the like. A bodily fluid can also include fecal material. Environmental samples are, e.g., soil, sludge, water, and the like. The sample can be processed, e.g., centrifuged, extracted, and/or lysed if cells are present. Alternatively, the sample can be directly placed in contact with the membrane.

Analyte-specific binding to the analyte-specific binding agent can be detected using any suitable detector. In general, the detector is composed of an illumination source and detection electronics. The simplest types of light sources include light emitting diodes (LEDs), laser, laser diodes, and filament lamps. These sources can be used in conjunction with optical filters, diffraction gratings, prisms, and other optical components to provide a specified spectral component of light. Alternative forms of radiation such as bioluminescence, fluorescence, and others could also be employed. Although typical fluorophores require excitation wavelengths in the visible portion of the spectrum (300-700 nm wavelength), other wavelengths in the infrared and ultraviolet portion of the spectrum could also prove useful for illuminating the binding agents on the membrane. The absorbed, reflected, or re-emitted light can then be propagated to an optical apparatus for detection, using photosensitive detectors such as photodiodes or photomultiplier tubes, in combination with some type of spectral and/or spatial filtering. Spatial filtering of the light is possible by either transverse scanning of the membrane or with two-dimensional detectors such as charge coupling device cameras (CCDs) and video cameras.

An example of a suitable detector is a reflectometer which measures the reflectance of reflecting surfaces. The reflectometer can use a light source which provides a full or partial spectrum of electromagnetic radiation. An exemplary light source is composed of LEDs which provide wavelengths of 430 nm (blue), 565 nm (green), 640 nm (red) and 880 nm (infrared) and is current based to accommodate manufacturing variations. LEDs of this type are available from Fairchild Semiconductor (Irving, Tex.). The detector for the reflectometer can be capable of both broad-spectrum and narrow spectrum sensitivity (individual RGB colors). The detector and measurement can be implemented in such a manner as to reduce sensitivity to power supply and coupled noise. A commercially available detector of this type is available from Texas Advanced Optoelectronic Solutions Inc. (Plano, Tex.).

Alternatively, the detector can be a camera or imaging device which has adequate lighting and resolution for spatially resolving individual signals produced by the second, labeled binding agents. Miniature cameras are commonly found in devices such as cellular phones and endoscopic tools. In this regard, an imaging device of the present invention can be any known in the art that is compatible with the various designs and configurations of the instant apparatus. For example, the camera can employ any common solid state image sensor including a charged coupled device (CCD), charge injection device (CID), photo diode array (PDA), or complementary metal oxide semiconductor (CMOS), which offers functionality with simplified system interfacing. For example, a particularly suitable CMOS imager including active pixel-type arrays is disclosed in U.S. Pat. No. 5,471,515. This CMOS imager can incorporate a number of other different electronic controls that are usually found on multiple circuit boards of much larger size. For example, timing circuits, and special functions such as zoom and anti-jitter controls can be placed on the same circuit board containing the CMOS pixel array without significantly increasing the overall size of the host circuit board. Furthermore, this particular CMOS imager requires 100 times less power than a CCD-type imager. The CMOS imager disclosed in U.S. Pat. No. 5,471,515 has enabled the development of a "camera on a chip." As such, many CMOS imagers can be manufactured at a fraction of the cost of other solid state imaging technologies. Suni Microsystems, Inc. (Mountain View, Calif.) has also developed a CCD/CMOS hybrid which combines the high quality image processing of CCDs with standard CMOS circuitry construction. The image sensor can also employ a lens to focus the optical signals. Furthermore, to increase depth of field and reduce ambient light noise, an aperture can be used.

Data Integration, Analysis, Storage, and Transmission. The present apparatus also provides a computer, which integrates the detected analyte-specific binding with the data acquired by any one of the plurality of data acquisition components. The binding and data thus integrated (i.e., brought together) can then be analyzed and stored (either long-term or short-term) by the computer for subsequent access by the user. Desirably, the on-board computer has an internal operating system that accesses one or more algorithms and/or computer software to analyze data from the assay component to determine the presence and/or quantity of analyte(s) that is being tested. By "analyze", it is meant that the instant apparatus can do more than merely display an assay measurement value. For example, charts, plots and graphs of compiled data (e.g., standard curves for quantifying analytes) can be generated and additional factors such as data acquired from peripheral data acquisition components can be used to process and/or display information relating to the sample being tested or source of the sample. The algorithm or algorithms used are developed based upon the parameters in which the apparatus will be used. Additionally, if a software element is used, it may be adjusted as needed such that the apparatus becomes simpler and/or more accurate in determining the presence and/or quantity of analyte(s) present in the sample. The type of algorithm used can be based upon a variety of factors, either alone or in combination and including, but not limited to, the analyte to be detected, the type of assay component used, the sample to be tested, the image generated, the size of the features in the image, the image and/or feature sizes and/or shapes in that pattern, and the desired level of sensitivity, among others.

The acquired, integrated and analyzed data can be stored in computer memory in any form, e.g., EEPROM, RFID, RAM, ROM, EPROM or other form of static or dynamic memory. Any type of computer chip including a memory can be affixed to, or otherwise associated with, the apparatus. For example, removable memory "sticks" or "cards" (e.g., a SIM card) can be used, providing unlimited data capacity. SIM cards are particularly suitable as they provide data encryption in addition to data storage. Moreover, SIM cards provide both an antenna and a transceiver to send and receive information. As many conventional hand-held electronic devices employ SIM cards, SIM cards are readily available from a variety of commercial sources.

Raw data and/or integrated and analyzed data are displayed on a display screen. The display screen can be any commercially available unit used in conventional cell phones, PDA and the like. For example, the display screen can be a 128×64 bit graphic LCD display with integral backlight, wherein the backlight is controlled by the on-board computer. Such LCD displays are commercially available from sources such as MicroTips Technology, Inc. (Orlando, Fla.).

Preferably, a large portion of the display screen is used to display data. However, as indicated above, the display screen can also provide touch-responsive areas so that, such as is known in the art, touching those areas will be recognized by the apparatus and interpreted to modify what is displayed on the screen.

Power to the apparatus can be supplied by an external source (e.g., via a tether), internal batteries, or other power source including one or more power cells. A battery can be one or more standard power cells, for example alkaline, lithium, nickel-cadmium; or a molded polymeric or elastomer battery which could be shaped to fit within the housing of the apparatus. Alternatively, magnetic induction is another possible source of power, as is piezoelectrics. In addition, one of skill in the art could adapt other power sources such as fluid dynamic, solar or the like to power the instant apparatus. The apparatus can contain a battery which is sealed within the apparatus (i.e., not user replaceable) to provide power to the LCD, backlight and detector. Rechargeable or user replaceable batters can also be provided as can a back-up battery (e.g., a primary lithium coin cell) to maintain time. Charging circuitry can also be integrated into a docking device.

Other embodiments of the present apparatus include a timer for timing the assay, one-point assay calibration, memory stick compatibility for software upgrades, and an annunciator which provides light, vibration and/or sound output means for user feedback. Feedback could be, for example, acknowledging to the user that an attempted data acquisition was successful. This output signal may also be used to acknowledge error status, a full memory and/or a cleared memory on the apparatus. An LED provides an extremely low power consuming and rugged output means for user feedback.

A barcode reader is also provided for automatically entering information about the assay component. Such a barcode reader could read codes including ISBN, UPC-E, UPC-A, EAN-8, EAN-13, Code 39, and/or Code 128. Such barcode readers are well-known and commercially available. The barcode reader can be combined with a barcode activation system which identifies the test to be analyzed and automatically initiates one-point assay calibration of that particular test, thereby precluding mistakes by the user or erroneous results by the apparatus. Each individual assay component would contain a unique barcode which would be read and used to initialize the apparatus such that the appropriate algorithm(s) would be employed.

It is contemplated that a variety of input and outputs can be provided to and from the apparatus, e.g., via port(s) 36 and output interface 42. These outputs and inputs may include, for example, digital inputs, digital outputs, analog inputs, analog outputs, serial communications (e.g., to a printer, modem or host computer), and network, such as Ethernet, communications. Such communications can also include wireless data transfer using such technologies as BLUETOOTH, HomeRF, IEEE P802.15 or proprietary protocols in the 900 megahertz, 2.4 gigahertz or other frequency band.

The instant apparatus can be configured to attach to a host computer thereby using the host computer to obtain power, storage, direct download and software control functionality and updates. The connection to the host computer can be by any means providing direct connection to the host computer's bus. For example, an apparatus can be built into or have a connection via a PCMCIA card, PC card, flash card, USB or proprietary connection, for example to a PDA, cell phone or optical mouse. The connection can be a direct electromechanical connection (cable or contacts, e.g., via port 36) or a wireless connection such as an optical connection. Transfer of information between the apparatus and a host computer can also be achieved using a docking device which can accept the apparatus. The docking device can be an optical reader which accepts optical output from a key fob in the form of light or other wavelength signals (IrDA, infra red, sound, RF, visible light) which transmit the information contained in the memory of the apparatus. The docking device would then be capable of transmitting the received information to a computer device by direct connection, RF, or light signals (IrDA, visible light, or fiber optic).

The docking device cable can be connected to the host computer by any available transmission standard or proprietary I/O port (serial, parallel, USB, audio input, PCMCIA, IDE, ISA, PCI, SCSI, FIREWIRE, optical), including the keyboard port. In some embodiments, the docking device is in the form of a mouse device or other computer peripheral with a mating cavity which the instant apparatus fits into. Built into a cell phone or PDA, the docking means can be an optical emitter/detector, Irda port or RFID interrogator circuitry.

In particular embodiments of the present invention, data being transferred between peripheral components and the instant apparatus as well as between the apparatus and a host computer is encrypted, in particular when wireless data transfer is employed. In this regard, the present also provides for encryption and decryption modules to encrypt and decrypt information in compliance with HIPAA.

An advantage of the present apparatus is that tests can be run on a wide variety of analytes and a variety of different samples can be analyzed with results obtained within minutes or seconds. Moreover, when a plurality of binding agents is employed in the instant assay component, the apparatus can use this data along with data from a plurality of data acquisition components to provide a differential diagnosis of diseases or disease states or conditions, as well as the identification of specific contaminants in biological and environmental samples. Thus, in the clinical setting the present invention can provide a quick and accurate diagnosis during a patient visit, shortening the decision time to medical intervention and minimizing the need for additional patient follow-up, thereby reducing overall health care delivery costs. Furthermore, the instant apparatus can be employed to monitor patient compliance. Moreover, given the portability of the present apparatus, data acquisition, integration, analysis and transmission can be carried out in remote locations.

What is claimed is:

1. An improved sample analysis apparatus of the type having a removable component with (a) a membrane, said membrane having an upper and lower surface, (b) an analyte-specific binding agent attached to said membrane, (c) a means for absorbing liquid located adjacent to the lower surface of said membrane, and (d) a piston means located adjacent to said means for absorbing liquid, wherein said piston means draws analytes in a sample through the membrane into the means for absorbing liquid, the improvement comprising
   a chamber for housing at least two removable components in their entirety,
   a detector adjacent to said chamber and arranged to detect analyte-specific binding to the analyte-specific binding agent on the upper surface of membranes of the at least two removable components housed in their entirety in the chamber,
   a plurality of data acquisition components for acquiring data, and
   a computer, wherein the computer integrates, analyzes and stores the detected analyte-specific binding and acquired data thereby providing improved sample analysis.

2. The apparatus of claim 1, wherein the apparatus comprises one or a plurality of analyte-specific binding agents.

* * * * *